United States Patent
Lin et al.

(10) Patent No.: US 11,832,897 B2
(45) Date of Patent: Dec. 5, 2023

(54) METHOD AND SYSTEM FOR SURGICAL NAVIGATION

(71) Applicant: Remex Medical Corp., Taichung (TW)

(72) Inventors: Chen-Tai Lin, Taichung (TW); Shan-Chien Cheng, Taichung (TW); Ying-Yi Cheng, Taichung (TW)

(73) Assignee: Remex Medical Corp., Taichung (TW)

( * ) Notice: Subject to any disclaimer, the term of this patent is extended or adjusted under 35 U.S.C. 154(b) by 0 days.

(21) Appl. No.: 17/389,747

(22) Filed: Jul. 30, 2021

(65) Prior Publication Data
US 2023/0034038 A1   Feb. 2, 2023

(51) Int. Cl.
| | | |
|---|---|---|
| G06T 15/08 | (2011.01) | |
| G06T 19/00 | (2011.01) | |
| A61B 34/20 | (2016.01) | |
| G06T 11/60 | (2006.01) | |
| A61B 90/00 | (2016.01) | |

(52) U.S. Cl.
CPC .............. *A61B 34/20* (2016.02); *A61B 90/37* (2016.02); *G06T 11/60* (2013.01); *A61B 2034/2065* (2016.02); *A61B 2090/364* (2016.02); *A61B 2090/3762* (2016.02); *A61B 2090/3916* (2016.02); *G06T 2210/41* (2013.01)

(58) Field of Classification Search
CPC ............ A61B 34/20; A61B 2034/2065; A61B 2090/364
USPC ........................................................ 345/634
See application file for complete search history.

(56) References Cited

U.S. PATENT DOCUMENTS

| | | | | |
|---|---|---|---|---|
| 8,730,237 | B2 * | 5/2014 | Ruijters | G06T 19/00 |
| | | | | 382/128 |
| 9,987,024 | B2 * | 6/2018 | Frey | A61B 17/1703 |
| 2014/0206990 | A1 * | 7/2014 | Epstein | A61B 90/37 |
| | | | | 600/587 |
| 2017/0258526 | A1 * | 9/2017 | Lang | H05K 999/99 |
| 2018/0049839 | A1 * | 2/2018 | Seong | A61B 90/11 |
| 2018/0132940 | A1 * | 5/2018 | Kao | G06F 3/0482 |
| 2018/0199998 | A1 * | 7/2018 | Chen | G06F 3/04815 |
| 2018/0263714 | A1 * | 9/2018 | Kostrzewski | A61B 17/1703 |
| 2019/0005848 | A1 * | 1/2019 | Garcia Kilroy | A61B 1/00042 |
| 2021/0085268 | A1 * | 3/2021 | Alexandroni | A61B 90/39 |

FOREIGN PATENT DOCUMENTS

| | | | | |
|---|---|---|---|---|
| CN | 106308919 B | | 1/2017 | |
| TW | 1618036 B | | 3/2018 | |
| TW | 1654963 B | | 4/2019 | |
| WO | WO-2015003224 A1 * | | 1/2015 | ......... A61B 17/1703 |
| WO | WO-2019148154 A1 * | | 8/2019 | ............ A61B 34/10 |
| WO | WO-2021162287 A1 * | | 8/2021 | |
| WO | WO-2022132730 A1 * | | 6/2022 | |

* cited by examiner

*Primary Examiner* — Javid A Amini
(74) *Attorney, Agent, or Firm* — CKC & Partners Co., LLC

(57) ABSTRACT

A surgical navigation method includes selecting one or more two-dimensional images from a three-dimensional image. The method further includes adjusting a portion of the two-dimensional images along a viewing direction. The method also includes superimposing the portion of the two-dimensional images along the viewing direction to form a two-dimensional superimposed image. The method further incudes guiding movement of a virtual surgical instrument into the two-dimensional superimposed image.

19 Claims, 7 Drawing Sheets

METHOD AND SYSTEM FOR SURGICAL NAVIGATION

BACKGROUND

Field of the Invention

The present invention generally relates to methods and systems for surgical navigation, and in particular, methods and systems relating to the manipulation of radiographic imagery to provide a more efficient and accurate method for directing surgical tools.

Background of the Invention

Surgical navigational methods and systems help medical staff locate body parts of a patient (such as, e.g., osseous and soft tissue structures) and guide and place medical surgical instruments, and can perform implant placement surgery (such as, e.g., screws) into the body parts. Surgeons may use utilize radiographic images, such as an X-ray scan or a computed tomography (CT) scan, to help locate certain targets in a patient's body. For example, in a case involving the placement of a screw into a patient's spine, a surgeon may observe an X-ray image of the patient's spine to help guide the correct placement of the screw. However, there are deficiencies with such conventional surgical navigation systems. For example, whether using X-ray or CT imagery, certain anatomical structures (such as a pedicle on a patient's spine) may be difficult to locate, which may lead to extra time in the operating room to correctly place surgical instruments. In turn, extended time in the operating room can lead to complications with anesthesia, a greater risk developing an infection, higher risk for developing a blood clot, and an overall poorer patient outcome. Additionally, difficulty in locating correct anatomical structures may lead to errors in surgical instrument placement. This can result in the need for additional corrective surgeries.

In an attempt to address these deficiencies, surgeons and other medical personnel have resorted to obtaining additional radiographic scans in hopes of obtaining a clearer view of the desired anatomical structure. This approach, however, can be time consuming and result in additional financial costs. Additionally, this approach requires the patient to submit to multiple radiographic scanning procedures, which may harm the patient by increasing the patient's lifetime X-ray exposure (causing an increased risk for developing cancers).

In view of the foregoing, it is desirable to reduce the time and increase the accuracy of identifying anatomical structures in surgical patients. For example, there is a need for an improved method and system to utilize imagery that can more consistently and reliably identify anatomical structures.

SUMMARY OF THE DISCLOSURE

According to an embodiment of the present disclosure, a surgical navigation method includes selecting one or more two-dimensional images from a three-dimensional image; adjusting a portion of the two-dimensional images along a viewing direction; superimposing the portion of the two-dimensional images along the viewing direction to form a two-dimensional superimposed image; and guiding movement of a virtual surgical instrument into the two-dimensional superimposed image.

According to various embodiments of the present disclosure, the three-dimensional image may be a computed tomography scan.

According to various embodiments of the present disclosure, the viewing direction may be defined in a coronal, sagittal, or axial plane.

According to various embodiments of the present disclosure, the portion of the two-dimensional images may include a pedicle of a spinal vertebra.

According to various embodiments of the present disclosure, the two-dimensional superimposed image may include a pedicle of a spinal vertebra.

According to some embodiments, the portion of the two-dimensional images is a first portion and the two-dimensional superimposed image is a first two-dimensional superimposed image, and the method further includes adjusting a second portion of the two-dimensional images along a second viewing direction, the second viewing direction being different from the first viewing direction; superimposing the second portion of the two-dimensional images along the second viewing direction to form a second two-dimensional superimposed image; and guiding movement of the virtual surgical instrument into the first and second two-dimensional superimposed images.

According to some embodiments, the method further includes adjusting a third portion of the two-dimensional images along a third viewing direction, the third viewing direction being different from the first and second viewing directions; superimposing the third portion of the two-dimensional images along the third viewing direction to form a third two-dimensional superimposed image; and guiding movement of the virtual surgical instrument into the first, second, and third two-dimensional superimposed images.

According to some embodiments, the method further includes displaying the first and second two-dimensional superimposed images on a display device.

According to some embodiments, the method further includes displaying the first, second, and third two-dimensional superimposed images on a display device.

According to another embodiment of the present disclosure, a surgical navigation system includes a memory device, controller, and display device. The memory is configured to store a three-dimensional image. In some embodiments, the controller is configured to select one or more two-dimensional images from the three-dimensional image; select a portion of the two-dimensional images along a viewing direction; superimpose the portion of the two-dimensional images along the viewing direction to form a two-dimensional superimposed image; and guide a virtual surgical instrument into the two-dimensional superimposed image. The display device is configured to display the two-dimensional superimposed image.

According to some embodiments, the system further includes an optical tracker configured to track the virtual surgical instrument and an anatomical region of a patient; wherein the controller is further configured to: receive a surgical instrument tracking signal and an anatomical region tracking signal from the optical tracker; and send instructions to the display device to display the virtual surgical instrument on the two-dimensional superimposed image, the virtual surgical instrument positioned and oriented with respect to the anatomical region in a manner corresponding to a position and orientation of the surgical instrument with respect to the anatomical region.

According to another embodiment of the present disclosure, a computer-readable storage medium has instructions, which when executed on a computer processor, causes the processor to perform a surgical navigation method including the steps of selecting one or more two-dimensional image from a three-dimensional image; selecting a portion of the two-dimensional images along a viewing direction; superimposing the portion of the two-dimensional images along the viewing direction to form a two-dimensional superimposed image; and guiding movement of a virtual surgical instrument into the two-dimensional superimposed image.

The below descriptions of the various embodiments of the surgical navigation method and system uses placement of a spinal screw into a pedicle of a spine as an illustrative example. It should be noted that the embodiments of the present disclosure can be applied to any anatomical structure of the human body, including both osseous and soft tissue structures. According to some embodiments, the type of radioactive imaging used is determined, e.g., by the type of anatomical structure being targeted. For example, X-ray and CT scans may be used for osseous structures, magnetic resonance imaging (MRI) may be used for soft tissue structures, and positron emission tomography (PET) scans may be used for tumors.

According to embodiments of the present disclosure, the surgical navigation method and system may be for cortical bone trajectory (CBT) screw placement and allows the outer contour of a pedicle in a spinal image to be very clearly and easily identified. This may enable the medical staff to correctly fix a screw in the pedicle when referencing this spinal image. In addition, quickly and efficiently obtaining clear presentation of the pedicle contour may greatly shorten the time for medical staff to find and determine an implantation position and path. This thereby improves the safety of an operation and solves the problems that using conventional navigation technologies/techniques to find the position of the pedicle presents (need to rely on experience, increased searching time, and propensity for positioning errors).

BRIEF DESCRIPTION OF THE DRAWINGS

The accompanying drawings, which are incorporated in and constitute a part of this disclosure, illustrate various embodiments and aspects of the present disclosure. In the drawings.

DETAILED DESCRIPTION

Figure 1:
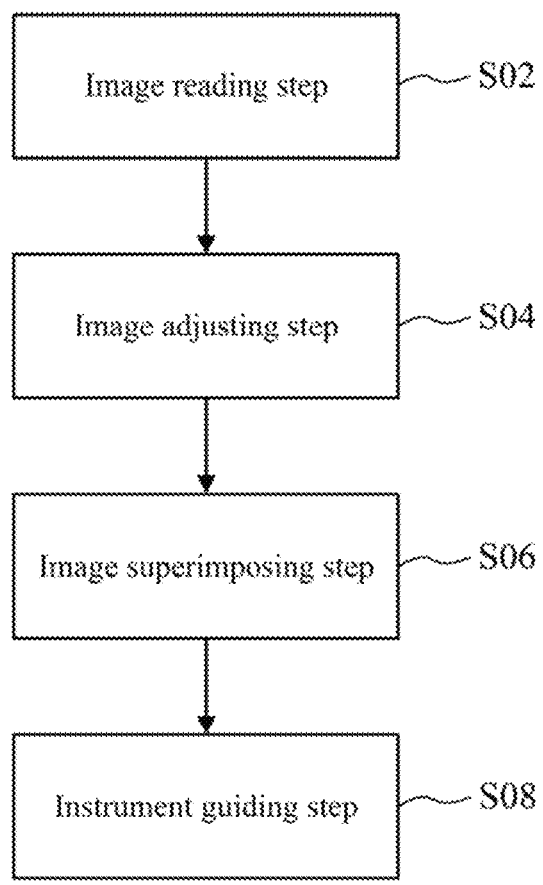
FIG. 1 is a schematic flowchart illustrating a surgical navigation method according to an embodiment of the present disclosure.

The following detailed description refers to the accompanying drawings. Wherever possible, the same reference numbers are used in the drawings and in the following description to refer to the same or similar parts. While several exemplary embodiments and features of the invention are described herein, modifications, adaptations, and other implementations are possible without departing from the spirit and scope of the invention. For example, substitutions, additions, or modifications may be made to the components illustrated in the drawings, and the exemplary methods described herein may be modified by substituting, reordering, or adding steps to the disclosed methods. Accordingly, the following detailed description does not limit the invention. Instead, the proper scope of the invention is defined by the appended claims.

In addition, when a component (or apparatus or module, etc.) is "connected/linked to" another component, it may mean that the component is directly connected/linked to the another component, or it may mean that a certain component is indirectly connected/linked to another component, i.e., there are other components between the component and the another component. When it is dearly stated that a certain component is "directly connected/linked" to another component, it means that there is no other component between the component and the another component. The terms "first", "second", "third", etc. are only used to describe different components, and there are no restrictions on the components themselves. Therefore, the first component may also be renamed the second component. In addition, a combination of components/apparatuses/circuits herein is not a commonly known, conventional or well-known combination in the art. Whether components/units/circuits themselves are well-known cannot be used to determine whether the combination relationship thereof is easily completed by a person of ordinary skill in the art.

FIG. 1 is a schematic flowchart illustrating a surgical navigation method 100 according to an embodiment of the present disclosure. The surgical navigation method 100 is used for guiding a virtual surgical instrument and includes an image reading step S02, an image adjusting step S04, an image superimposing step S06, and an instrument guiding step S08.

In accordance with some embodiments of the present disclosure, the image reading step S02 includes reading a three-dimensional image (such as, e.g., an image of a spine), from a memory. The three-dimensional image includes one or more two-dimensional images, and the two-dimensional images may be obtained through scanning along at least one cutting direction. In accordance with some embodiments, the image adjusting step S04 includes selecting a part or portion of one or more of the selected two-dimensional spinal images along at least one viewing angle direction, where the part of the two-dimensional spinal images contains a three-dimensional pedicle region.

In accordance with some embodiments of the present disclosure, the image superimposing step S06 includes superimposing the selected part of the two-dimensional spinal images (along the at least one viewing angle direction) to form a superimposed viewing direction image. The superimposed viewing direction image presents at least one two-dimensional superimposed region according to the at least one viewing angle direction, and the at least one two-dimensional superimposed region corresponds to the three-dimensional pedicle region.

In accordance with some embodiments of the present disclosure, the instrument guiding step S08 includes real time rendering the virtual surgical instrument in the at least one two-dimensional superimposed region of the superimposed viewing direction image according to the position of the surgical instrument. Therefore, according to the surgical navigation method 100, two-dimensional spinal images are superimposed and presented in a specific range. In accordance with some embodiments, utilizing this superimposed viewing direction image helps distinguish a pedicle contour because the outer layer of the pedicle is of high density bone and high density bone appears bright white in the image. Depending on the viewing angle direction chosen, a coronal plane contour, a sagittal plane contour or a axial plane contour of pedicle can be clearly identified in the image allowing for efficient application of a CBT screw implantation technique. Medical staff may correctly fix a screw in the pedicle using the superimposed viewing direction image and can greatly shorten the time for medical staff to find and determine an implantation position and path, thereby improving safety and patient outcomes. The following description provides detailed embodiments to illustrate the details of the above steps.

Figure 2:
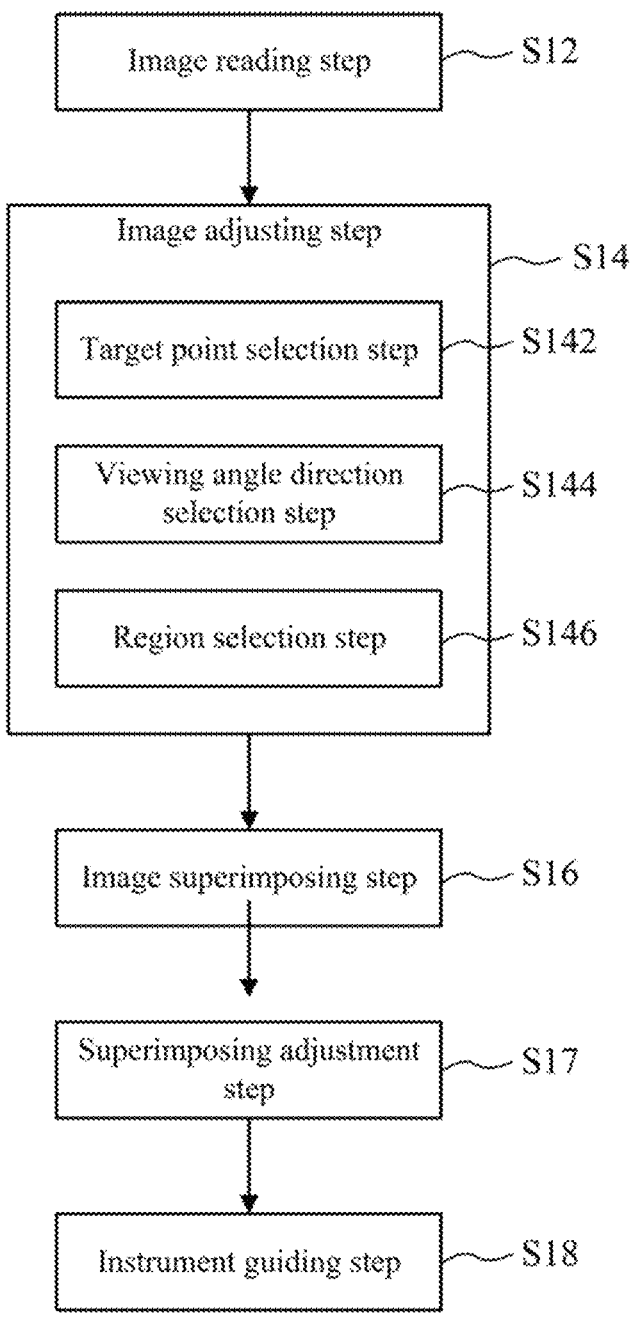
FIG. 2 is a schematic flowchart illustrating a surgical navigation method according to another embodiment of the present disclosure.
Figure 3:
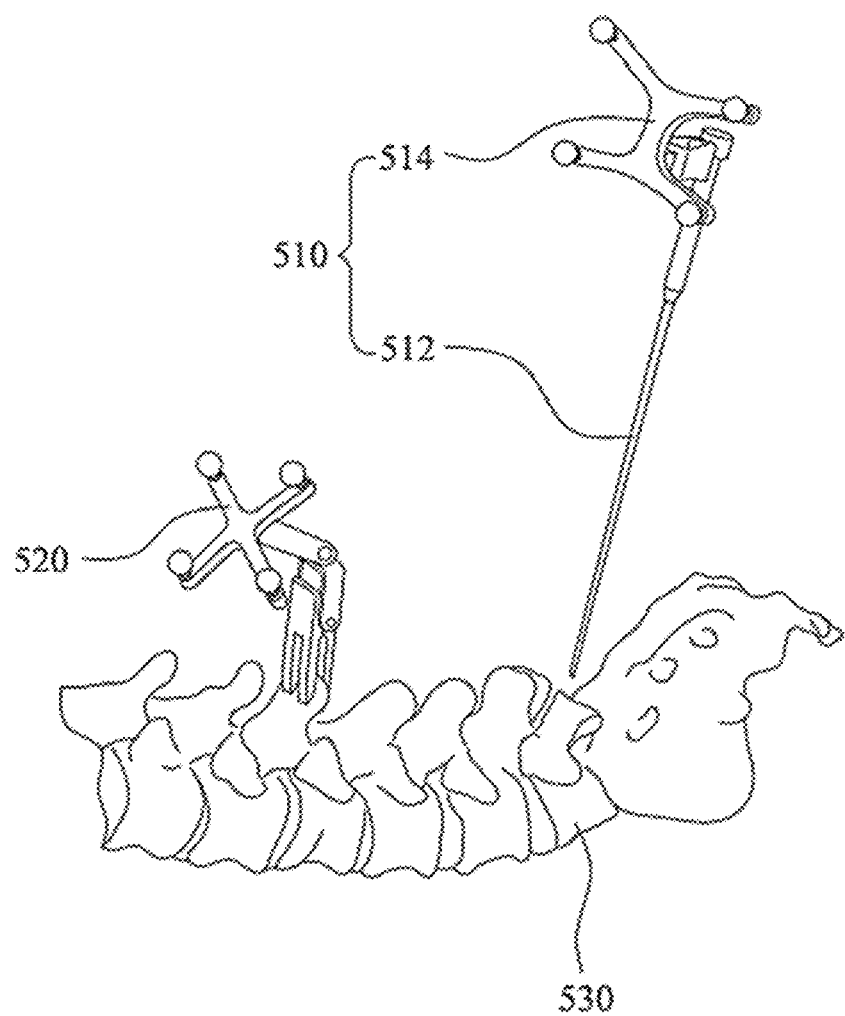
FIG. 3 is a schematic diagram illustrating the guiding of a virtual surgical instrument using the surgical navigation method of FIG. 2.
Figure 4:
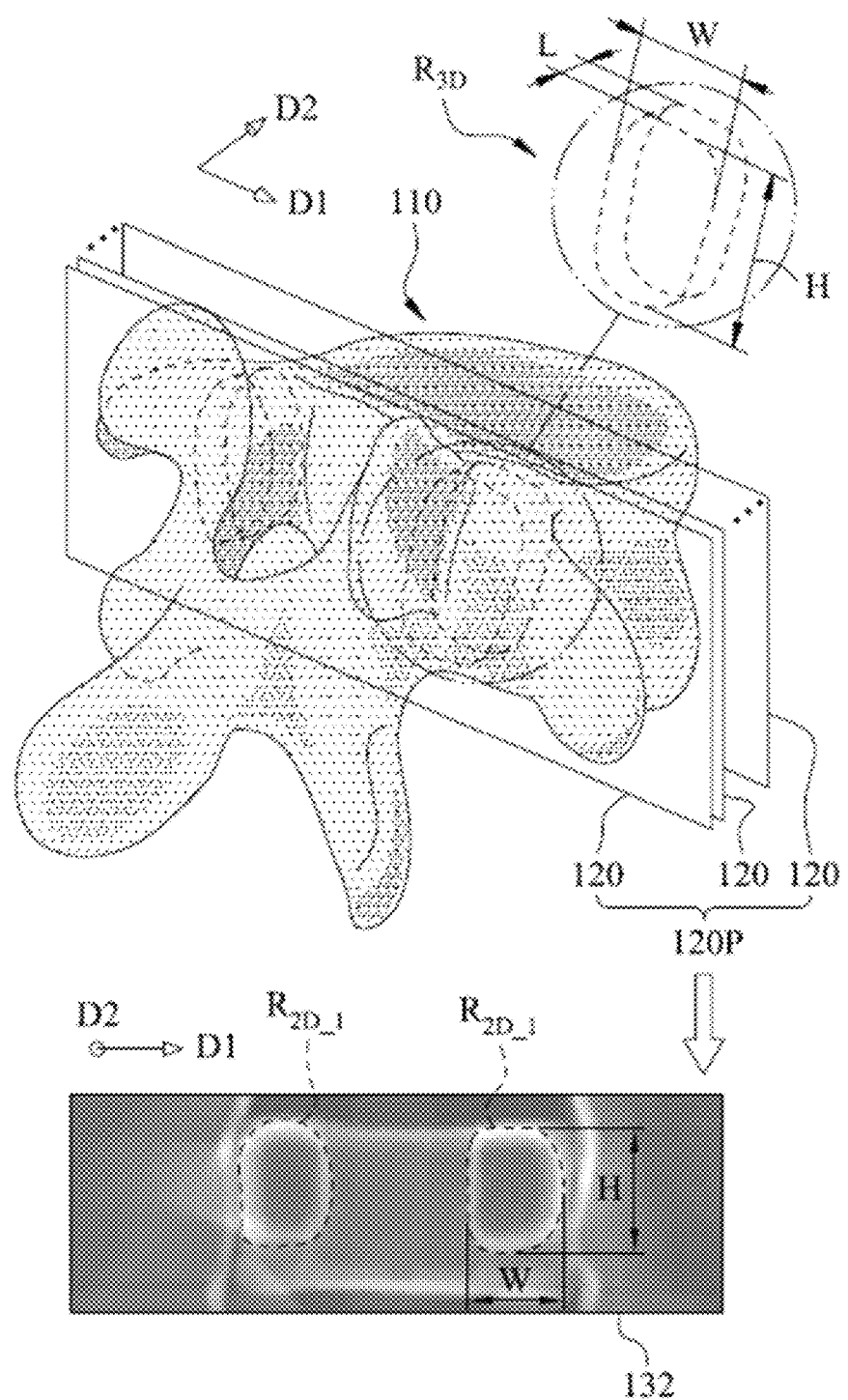
FIG. 4 is a schematic diagram illustrating superimposition at a spinal segment location corresponding to an image superimposing step of the surgical navigation method of FIG. 2.
Figure 5:
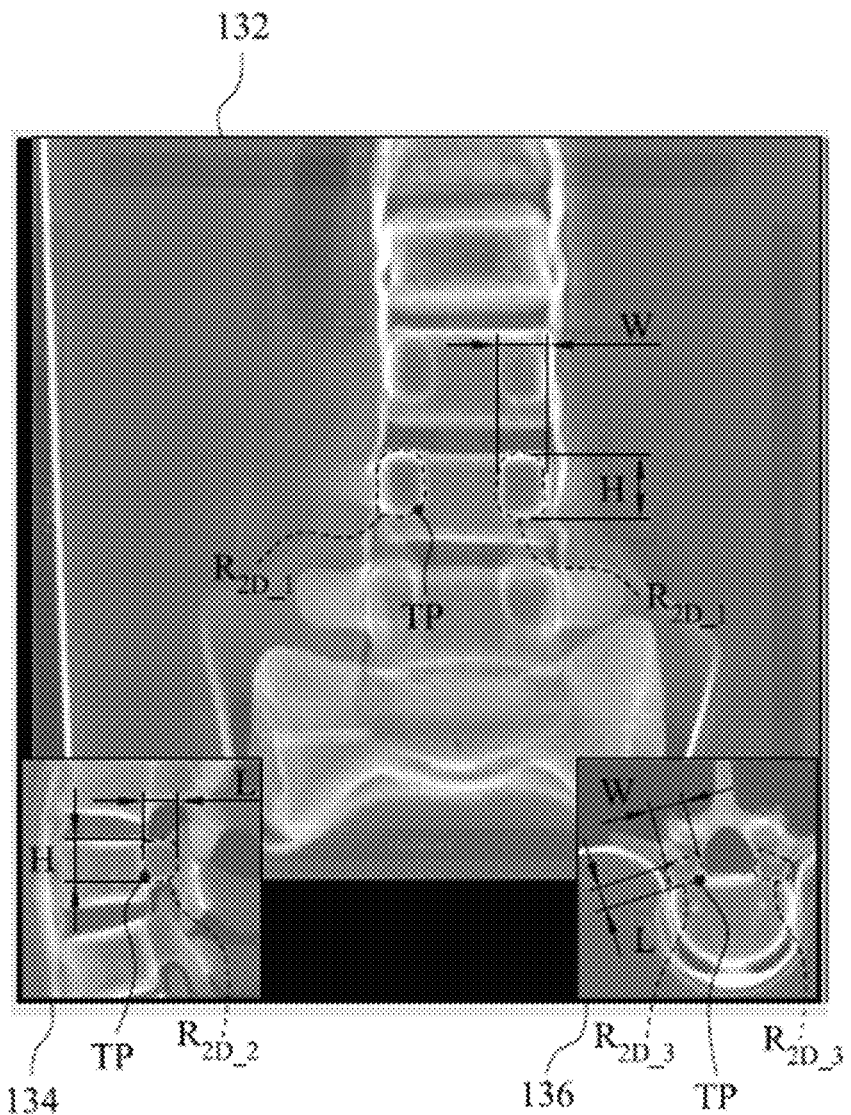
FIG. 5 is a schematic diagram illustrating a superimposed image in a first viewing direction generated in the surgical navigation method of FIG. 2.
Figure 6:
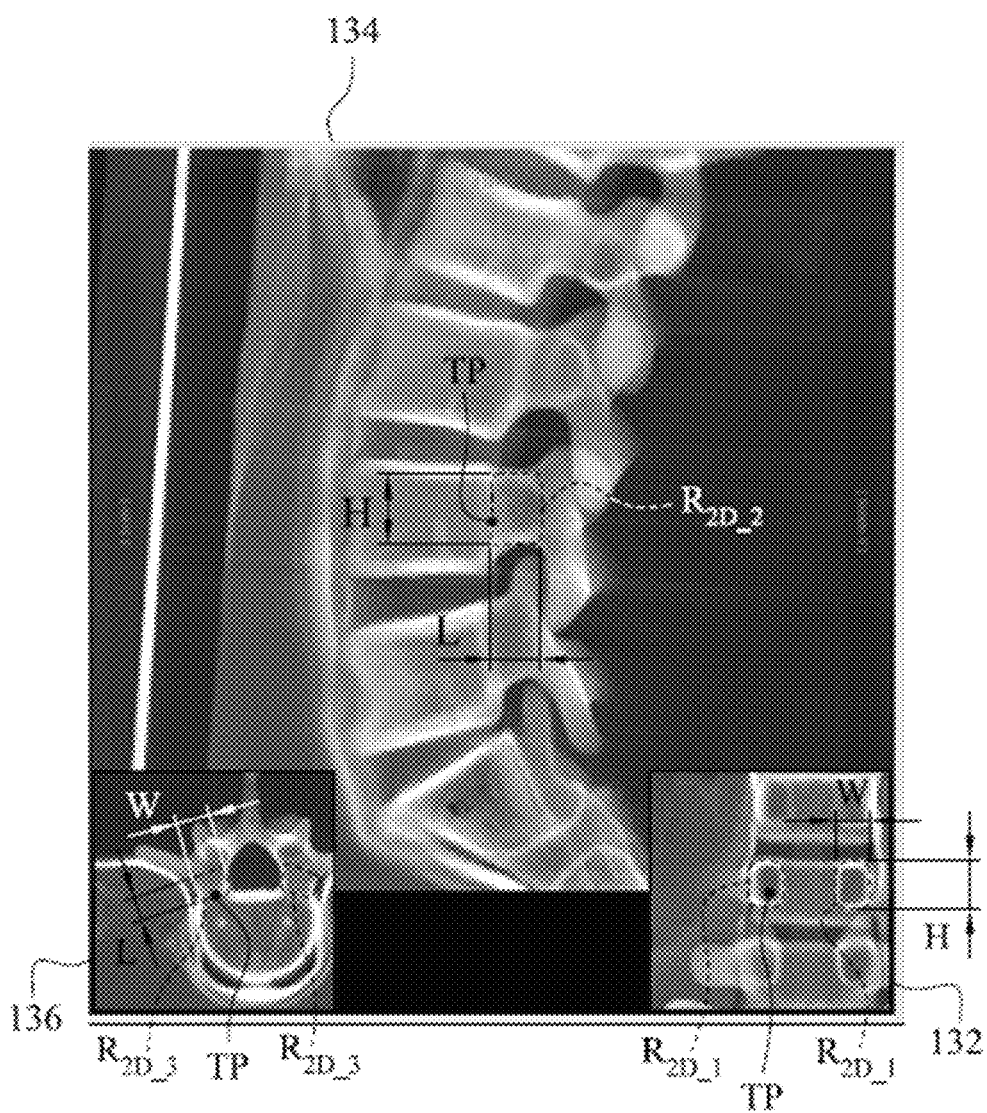
FIG. 6 is a schematic diagram illustrating a superimposed image in a second viewing direction generated in the surgical navigation method of FIG. 2.

FIG. 2 is a schematic flowchart illustrating a surgical navigation method 100a according to another embodiment of the present disclosure. FIG. 3 is a schematic diagram illustrating the guiding of a surgical instrument 512 by using the surgical navigation method 100a of FIG. 2. FIG. 4 is a schematic diagram illustrating the superimposing at a spinal segment in an image superimposing step S16 of the surgical navigation method 100a of FIG. 2. FIG. 5 is a schematic diagram illustrating a superimposed viewing direction image 130 of the surgical navigation method 100a of FIG. 2. FIG. 6 is a schematic diagram illustrating another superimposed viewing direction image 130a of the surgical navigation method 100a of FIG. 2.

In accordance with some embodiments of the present disclosure, the surgical navigation method 100a is used for guiding a virtual surgical instrument. The virtual surgical instrument may correspond to one surgical instrument 512 and may be displayed for the surgeon. The surgical navigation method 100a includes an image reading step S12, an image adjusting step S14, an image superimposing step S16, a superimposing adjustment step S17, and an instrument guiding step S18. In accordance with some embodiments, the image reading step S12, the image adjusting step S14, the image superimposing step S16, the superimposing adjustment step S17, and the instrument guiding step S18 may be applied in conjunction with a cortical bone trajectory (CBT) screw implantation technique where the virtual surgical instrument is a virtual screw, and the surgical instrument 512 is a screw. However, other virtual surgical instruments and surgical instruments 512 may be used.

In accordance with some embodiments of the present disclosure, the image reading step S12 includes reading a three-dimensional spinal image 110 from a memory, where the three-dimensional spinal image 110 includes two-dimensional spinal images 120, and the two-dimensional spinal images 120 are obtained through scanning along at least one cutting direction D1. In accordance with some embodiments, the three-dimensional spinal image 110 is a three-dimensional medical image generated through scanning of the spine by CT and reconstruction. During CT scanning, specific scanning parameters are used to obtain a required image. The scanning parameters include a layer thickness and a spacing, where the layer thickness denotes a section thickness of each two-dimensional spinal image 120, and the spacing denotes a distance between two adjacent two-dimensional spinal images 120. In other words, each two-dimensional spinal image 120 has a layer thickness, and there is a spacing between adjacent two of the two-dimensional spinal images 120.

In accordance with some embodiments of the present disclosure, the image adjusting step S14 includes selecting a part 120P of one or more of the two-dimensional spinal images 120 along at least one viewing angle direction D2, where the part 120P of the one or more two-dimensional spinal images 120 contains a three-dimensional pedicle region $R_{3D}$. In accordance with some embodiments, the image adjusting step S14 includes a target point selection step S142, a viewing angle direction selection step S144, and a region selection step S146, where the target point selection step S142 includes selecting a target point TP from the two-dimensional spinal images 120. The viewing angle direction selection step S144 includes selecting the at least one viewing angle direction D2 according to the two-dimensional spinal images 120. The region selection step S146 is to select the part 120P of the two-dimensional spinal images 120 along the at least one viewing angle direction D2 for the target point TP of the two-dimensional spinal images 120, where the part 120P of the two-dimensional spinal images 120 contains a three-dimensional pedicle region $R_{3D}$. Furthermore, the three-dimensional pedicle region $R_{3D}$ is columnar and has a pedicle length L, a pedicle width W, and a pedicle height H. The target point TP is close to the three-dimensional pedicle region $R_{3D}$.

In accordance with some embodiments of the present disclosure, the image superimposing step S16 includes superimposing the part 120P of the two-dimensional spinal images 120 along the at least one viewing angle direction D2 to form a superimposed viewing direction image 130, where the superimposed viewing direction image 130 presents at least one two-dimensional superimposed region (such as $R_{2D\_1}$, in FIG. 4 and $R_{2D\_1}$, $R_{2D\_2}$ and $R_{2D\_3}$ in FIGS. 5 and 6) according to the at least one viewing angle direction D2, and the at least one two-dimensional superimposed region corresponds to the three-dimensional pedicle region $R_{3D}$.

In accordance with embodiments of the present disclosure, the image superimposing step S16 is advantageous because high bone density regions appear white in a CT image, and because the pedicle surface density is high. Thus, the two-dimensional superimposed region corresponding to the three-dimensional pedicle region $R_{3D}$ can clearly identify the white pedicle contour in the picture. Additionally, different viewing angle directions D2, may generate different superimposed viewing direction images 130 and corresponding two-dimensional superimposed regions, such as a coronal plane contour, a sagittal plane contour or a axial plane contour of pedicle. In accordance with some embodiments, the number of the viewing angle directions D2 is the same as that of the two-dimensional superimposed regions and the number may be plural, and the viewing angle directions D2 may include (but not limited to) a first viewing angle direction, a second viewing angle direction, and a third viewing angle direction. The two-dimensional superimposed regions may include (but not limited to) a first two-dimensional superimposed region $R_{2D\_1}$, a second two-dimensional superimposed region $R_{2D\_2}$, and a third two-dimensional superimposed region $R_{2D\_3}$. The superimposed viewing direction image 130 may include (but not limited to) a superimposed coronal plane 132, a superimposed sagittal plane 134, and a superimposed axial plane 136. The target point TP is close to the first two-dimensional superimposed region $R_{2D\_1}$, the second two-dimensional superimposed region $R_{2D\_2}$, and the third two-dimensional superimposed region $R_{2D\_3}$.

In accordance with some embodiments of the present disclosure, the superimposed coronal plane 132 has a two-dimensional coronal coordinate system, where the superimposed coronal plane 132 presents one or two first two-dimensional superimposed regions $R_{2D\_1}$ according to the three-dimensional pedicle region $R_{3D}$ in the first viewing angle direction, and each first two-dimensional superimposed region $R_{2D\_1}$ has a pedicle height H, a pedicle width W, and a closed contour. The closed contour is the coronal plane contour of pedicle.

In accordance with some embodiments of the present disclosure, the superimposed sagittal plane 134 has a two-dimensional sagittal coordinate system, where the superimposed sagittal plane 134 presents one second two-dimensional superimposed region $R_{2D\_2}$ according to the three-dimensional pedicle region $R_{3D}$ in the second viewing angle direction, and the second two-dimensional superimposed region $R_{2D\_2}$ has a pedicle length L, a pedicle height H, and a sagittal plane contour of pedicle.

In accordance with some embodiments of the present disclosure, the superimposed axial plane 136 has a two-dimensional abscissa system, where the superimposed axial plane 136 presents one or two third two-dimensional superimposed regions $R_{2D\_3}$ according to the three-dimensional pedicle region $R_{3D}$ in the third viewing angle direction, and each third two-dimensional superimposed region $R_{2D\_3}$ has the pedicle length L, the pedicle width W, and an axial plane contour of pedicle. After the image superimposing step S16, the pedicle contour of the spinal segment corresponding to the target point TP in the superimposed viewing direction image 130 is the clearest.

In accordance with some embodiments of the present disclosure, the superimposing adjustment step S17 includes adjusting the number of the parts 120P of the two-dimensional spinal images 120 superimposed along at least one viewing angle direction D2 according to a contour sharpness of the two-dimensional superimposed regions in the superimposed viewing direction image 130.

In accordance with some embodiments of the present disclosure, the instrument guiding step S18 includes real-time rendering the virtual surgical instrument in the two-dimensional superimposed region of the superimposed viewing direction image 130 according to the position of the surgical instrument.

As shown in FIG. 4, in some embodiments, the viewing angle direction D2 of the superimposed coronal plane 132 may be the first viewing angle direction. In accordance with some embodiments, three-dimensional spinal images 110 generated by the CT scanning of one spinal segment along the cutting direction D1 corresponding to the first viewing angle direction include two-dimensional spinal images 120, and the part 120P of these two-dimensional spinal images 120 contains the three-dimensional pedicle region $R_{3D}$.

The two-dimensional spinal images 120 are superimposed to form a superimposed coronal plane 132. The superimposed coronal plane 132 presents one or two first two-dimensional superimposed regions $R_{2D\_1}$ according to the three-dimensional pedicle region $R_{3D}$ in the first viewing angle direction.

In some embodiments, as shown in FIG. 5 and FIG. 6, the viewing angle direction D2 of the superimposed sagittal plane 134 may be the second viewing angle direction. In accordance with some embodiments, three-dimensional spinal images 110 generated by the CT scanning of a plurality of spinal segments along the cutting direction D1 corresponding to the second viewing angle direction include two-dimensional spinal images, and the part of these two-dimensional spinal images covers the three-dimensional pedicle region $R_{3D}$.

The two-dimensional spinal images superimposed along the direction of the pedicle width W (i.e., the second viewing angle direction of the viewing angle direction D2), to form a superimposed sagittal plane 134. The superimposed sagittal plane 134 presents one or two second two-dimensional superimposed region $R_{2D\_2}$ according to the three-dimensional pedicle region $R_{3D}$ in the second viewing angle direction.

In accordance with some embodiments of the present disclosure, as shown in FIG. 5 and FIG. 6, the viewing angle direction D2 of the superimposed axial plane 136 may be the third viewing angle direction. In accordance with some embodiments, three-dimensional spinal images 110 generated by the CT scanning of one spinal segment along the cutting direction D1 corresponding to the third viewing angle direction include two-dimensional spinal images, and the part of these two-dimensional spinal images contains the three-dimensional pedicle region $R_{3D}$.

The two-dimensional spinal images superimposed along the direction of the pedicle height H (i.e., the third viewing angle direction of the viewing angle direction D2), to form a superimposed axial plane 136. The superimposed axial plane 136 presents one or two third two-dimensional superimposed region $R_{2D\_3}$ according to the three-dimensional pedicle region $R_{3D}$ in the third viewing angle direction.

There is no correlation between the operations of adjusting and superimposing images of FIG. 5 and FIG. 6. This means that the adjusting and superimposing images of FIG. 5 and FIG. 6 can be performed independently, such that medical staff can dearly understand the relative positions of the three-dimensional pedicle region $R_{3D}$ in different viewing angles.

In other embodiments, the number, layer thickness T and spacing S of the two-dimensional spinal image 120 of the three-dimensional spinal image 110, and the pedicle length L, pedicle width W, pedicle height H, cutting direction D1, viewing angle direction D2 and position of the target point TP of the three-dimensional pedicle region $R_{3D}$ can be changed according to actual conditions or demands, and the present disclosure is not limited to the above.

In accordance with embodiments of the present disclosure, only the part 120P of the two-dimensional spinal images 120 is superimposed in the present disclosure, which has a clearer local contour, compared with the full display of the two-dimensional spinal images 120 that would otherwise make it harder to focus on the point of interest.

Figure 7:
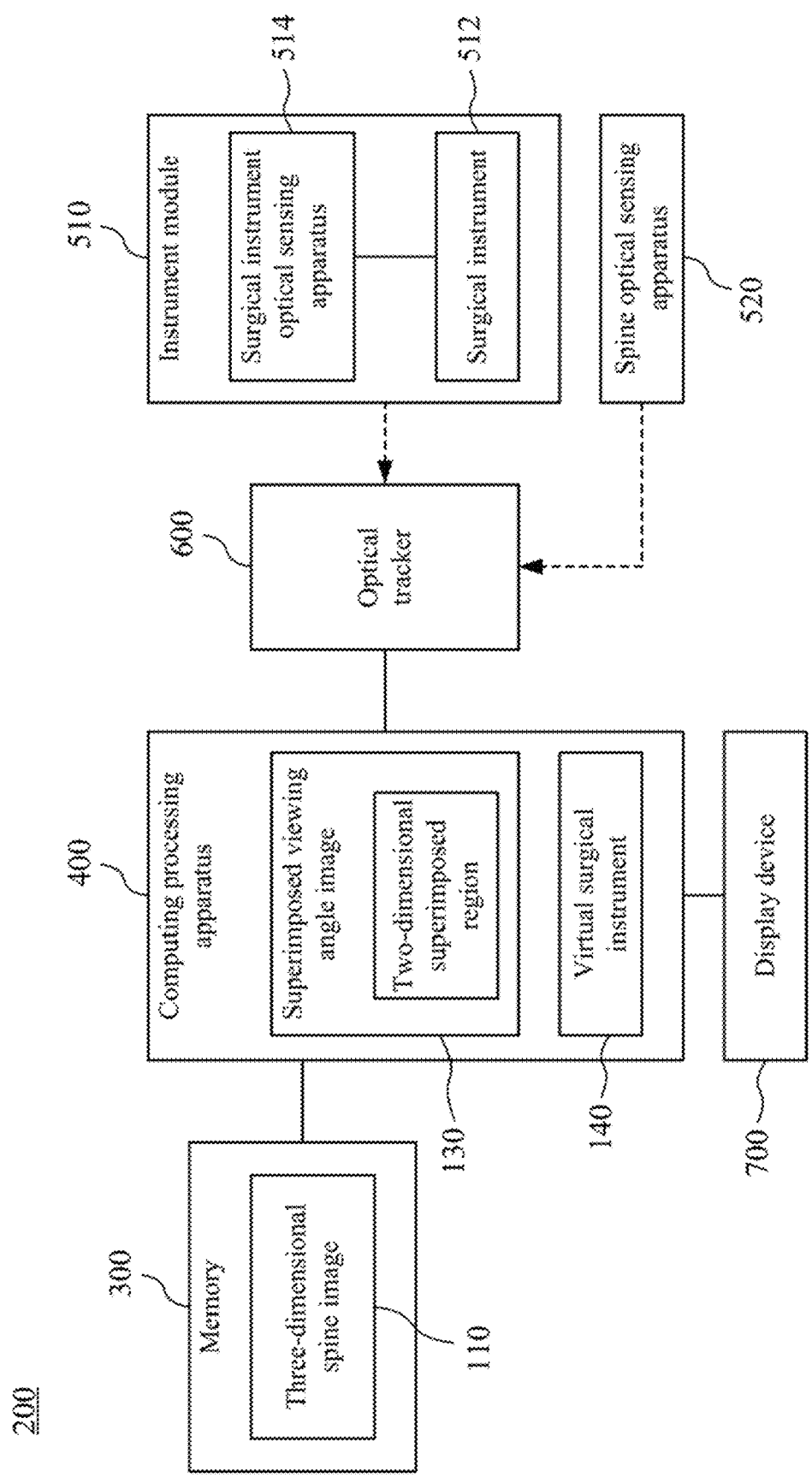
FIG. 7 is a schematic flowchart illustrating a surgical navigation method according to another embodiment of the present disclosure.

FIG. 7 is a schematic diagram illustrating a surgical navigation system 200 according to another embodiment of the present disclosure. The surgical navigation system 200 is configured to guide a virtual surgical instrument 140 and includes a memory 300, a processor 400, an instrument module 510, a spine optical sensing apparatus 520, an optical tracker 600, and a display device 700.

Although not shown, the various components of surgical navigation system 200 need not be fully contained within the user device. Each of the components may be physically separated from another and more than one of the components may be used to perform methods consistent with the present disclosure. Even though the components may be physically separated, the components may still be communicably connected by means of wired or wireless technology. For example, different components of system 100 and user device 105 may be connected through the Internet, a LAN (local area network), a WAN (wide area network), databases, servers, RF (radio frequency) signals, cellular technology, Ethernet, telephone, "TCP/IP" (transmission control protocol/internet protocol), and any other electronic communication format.

In accordance with some embodiments of the present disclosure, the memory 300 is configured to access a three-dimensional spinal image 110, where the three-dimensional spinal image 110 includes one or more two-dimensional spinal images 120, and the two-dimensional spinal images 120 are obtained through scanning along at least one cutting direction D1. The memory 300 may include all forms of computer-readable storage mediums such as non-volatile or volatile memories including, by way of example, semiconductor memory devices, such as EPROM, RAM, ROM, DRAM, EEPROM, and flash memory devices; magnetic disks such as internal hard disks and removable disks; magneto-optical disks; DVD disks, and CD-ROM disks. Memory device 300 may be used to store program code 305.

In accordance with some embodiments of the present disclosure, the processor 400 is electrically connected to the memory 300, where the computing processing apparatus 400 receives the three-dimensional spinal image 110 and is configured to perform operations including the following steps: an image reading step S02/S12, an image adjusting step S04/S14, an image superimposing step S06/S16, a superimposing adjustment step S17, and an instrument guiding step S08/S18 described above and shown in FIG. 1 to FIG. 6.

In accordance with some embodiments of the present disclosure, the processor 400 may be an ASIC (Application Specific Integrated Circuit) or it may be a general purpose processor. Processor 400 may include more than one processor. For example, processors may be situated in parallel, series, or both in order to process all or part of the computer instructions that are to be processed.

In accordance with some embodiments of the present disclosure, the instrument module 510 includes a surgical instrument 512 and a surgical instrument optical sensing apparatus 514, where the surgical instrument 512 is controlled and displaced by medical staff. The surgical instrument optical sensing apparatus 514 may be disposed on the surgical instrument 512, and includes a reflective ball and a fixing frame, and the fixing frame may be located between the reflective ball and the surgical instrument 512. The surgical instrument 512 may be a CBT screw, a guide probe or another surgical instrument, depending on the selection of medical staff and use conditions. The spine optical sensing apparatus 520 may be disposed on a spine 530 and includes a reflective ball and a fixing frame. The fixing frame may be located between the reflective ball and the spine 530. The optical tracker 600 may be electrically connected to the processor 400 and configured to track the spine 530 and the surgical instrument 512. When the medical staff control the surgical instrument 512, the surgical instrument optical sensing apparatus 514 may be facing to the optical tracker 600 so that the optical tracker 600 can track the surgical instrument 512 in real time. In addition, the spine optical sensing apparatus 520 may also be facing to the optical tracker 600 so that the optical tracker 600 can track the spine 530 in real time.

In accordance with some embodiments of the present disclosure, the display device 700 may be electrically connected to the processor 400, and displays a screen picture, and the screen picture presents the superimposed coronal plane 132, the superimposed sagittal plane 134, the superimposed axial plane 136 or the virtual surgical instrument 140 of the superimposed viewing direction image 130/130a. The display device 700 may be any conventional user interface display device. For example, display device 700 may include computer monitors, televisions, and LCD displays. Display device 700 may display GUI (Graphical User Interface) 705 which allows a user to interact with system 200 hardware and software applications.

The foregoing description has been presented for purposes of illustration. It is not exhaustive and does not limit the disclosure to the precise forms or embodiments disclosed. Modifications and adaptations of the disclosure will be apparent to those skilled in the art from consideration of the specification and practice of the disclosed embodiments of the disclosure.

Other embodiments of the disclosure will be apparent to those skilled in the art from consideration of the specification and practice of the disclosure herein. It is intended that the specification and examples be considered as exemplary only, with a true scope and spirit of the invention being indicated by the following claims.

What is claimed is:

1. A surgical navigation method comprising the steps of:
   selecting one or more two-dimensional images from a three-dimensional image;
   adjusting a portion of the one or more two-dimensional images along a viewing direction;
   superimposing the portion of the one or more two-dimensional images along the viewing direction to form a two-dimensional superimposed image; and
   guiding movement of a virtual surgical instrument into the two-dimensional superimposed image;
   wherein the two-dimensional superimposed image presents at least one two-dimensional superimposed region according to the viewing direction;
   wherein the method further comprises adjusting a number of images of the portion of the one or more two-dimensional images superimposed along the viewing direction according to a contour sharpness of the at least one two-dimensional superimposed region in the two-dimensional superimposed image;
   wherein the portion of the one or more two-dimensional images is a first portion, the two-dimensional superimposed image is a first two-dimensional superimposed image, the viewing direction is a first viewing direction, and the method further comprises:
     adjusting a second portion of the one or more two-dimensional images along a second viewing direction, the second viewing direction being different from the first viewing direction;
     superimposing the second portion of the one or more two-dimensional images along the second viewing direction to form a second two-dimensional superimposed image; and
     guiding movement of the virtual surgical instrument into the first and second two-dimensional superimposed images.

2. The surgical navigation method of claim 1, wherein the three-dimensional image is a computed tomography scan.

3. The surgical navigation method of claim 1, wherein the portion of the one or more two-dimensional images includes a pedicle of a spinal vertebra.

4. The surgical navigation method of claim 1, wherein the viewing direction is defined in a sagittal plane, a coronal plane, or an axial plane.

5. The surgical navigation method of claim 1, wherein the first and second two-dimensional superimposed images are displayed on a display device.

6. The surgical navigation method of claim 1, further comprising:
adjusting a third portion of the one or more two-dimensional images along a third viewing direction, the third viewing direction being different from the first and second viewing directions;
superimposing the third portion of the one or more two-dimensional images along the third viewing direction to form a third two-dimensional superimposed image; and
guiding movement of the virtual surgical instrument into the first, second, and third two-dimensional superimposed images.

7. The surgical navigation method of claim 6, wherein the first, second, and third two-dimensional superimposed images are displayed on a display device.

8. The surgical navigation method of claim 6, wherein the first viewing direction, the second viewing direction, and the third viewing direction are defined in a sagittal plane, a coronal plane, and an axial plane.

9. A surgical navigation system comprising:
a memory device configured to store a three-dimensional image;
a controller configured to
select one or more two-dimensional images from the three-dimensional image;
adjust a portion of the one or more two-dimensional images along a viewing direction; and
superimpose the portion of the one or more two-dimensional images along the viewing direction to form a two-dimensional superimposed image; and
guide a virtual surgical instrument into the two-dimensional superimposed image; and
a display device configured to display the two-dimensional superimposed image;
wherein the two-dimensional superimposed image presents at least one two-dimensional superimposed region according to the viewing direction;
wherein the controller is configured to adjust a number of images of the portion of the one or more two-dimensional images superimposed along the viewing direction according to a contour sharpness of the at least one two-dimensional superimposed region in the two-dimensional superimposed image;
wherein the portion of the one or more two-dimensional images is a first portion, the two-dimensional superimposed image is a first two-dimensional superimposed image, the viewing direction is a first viewing direction; and the controller is further configured to:
adjust a second portion of the one or more two-dimensional images along a second viewing direction, the second viewing direction being different from the first viewing direction;
superimpose the second portion of the one or more two-dimensional images along the second viewing direction to form a second two-dimensional superimposed image; and
guide the virtual surgical instrument into the first and second two-dimensional superimposed images.

10. The surgical navigation system of claim 9, wherein the three-dimensional image is a computed tomography scan.

11. The surgical navigation system of claim 9, wherein the portion of the one or more two-dimensional images includes a pedicle of a spinal vertebra.

12. The surgical navigation system of claim 9, wherein the two-dimensional superimposed image includes a pedicle of a spinal vertebra.

13. The surgical navigation system of claim 9, wherein the viewing direction is defined in a sagittal plane, a coronal plane, or an axial plane.

14. The system of claim 9, wherein the display device simultaneously displays the first and second two-dimensional superimposed images.

15. The surgical navigation system of claim 9, wherein the controller is further configured to:
adjust a third portion of the one or more two-dimensional images along a third viewing direction, the third viewing direction being different from the first and second viewing directions;
superimpose the third portion of the one or more two-dimensional images along the third viewing direction to form a third two-dimensional superimposed image; and
guide the virtual surgical instrument into the first, second, and third two-dimensional superimposed images.

16. The system of claim 15, wherein the display device simultaneously displays the first, second, and third two-dimensional superimposed images.

17. The system of claim 9 further comprising:
an optical tracker configured to track the virtual surgical instrument and an anatomical region of a patient;
wherein the controller is further configured to:
receive a surgical instrument tracking signal and an anatomical region tracking signal from the optical tracker; and
send instructions to the display device to display the virtual surgical instrument on the two-dimensional superimposed image, the virtual surgical instrument positioned and oriented with respect to the anatomical region in a manner corresponding to a position and orientation of the surgical instrument with respect to the anatomical region.

18. A computer-readable storage medium comprising instructions, which when executed on a computer processor causes the processor to perform a surgical navigational method, the method comprising the steps of:
selecting one or more two-dimensional images from a three-dimensional image;
adjusting a portion of the one or more two-dimensional images along a viewing direction;
superimposing the portion of the two-dimensional images along the viewing direction to form a two-dimensional superimposed image; and
guiding movement of a virtual surgical instrument into the two-dimensional superimposed image;
wherein the two-dimensional superimposed image presents at least one two-dimensional superimposed region according to the viewing direction;
wherein the method further comprises adjusting a number of images of the portion of the one or more two-dimensional images superimposed along the viewing direction according to a contour sharpness of the at least one two-dimensional superimposed region in the two-dimensional superimposed image;
wherein the portion of the one or more two-dimensional images is a first portion, the two-dimensional superimposed image is a first two-dimensional superimposed image, the viewing direction is a first viewing direction, and the method further comprises:
adjusting a second portion of the one or more two-dimensional images along a second viewing direction, the second viewing direction being different from the first viewing direction;

superimposing the second portion of the one or more two-dimensional images along the second viewing direction to form a second two-dimensional superimposed image; and guiding movement of the virtual surgical instrument into the first and second two-dimensional superimposed images.

19. A surgical navigation method comprising the steps of:

selecting one or more two-dimensional images from a three-dimensional image;

adjusting a portion of the one or more two-dimensional images along a viewing direction;

superimposing the portion of the one or more two-dimensional images along the viewing direction to form a two-dimensional superimposed image; and guiding movement of a virtual surgical instrument into the two-dimensional superimposed image;

wherein the two-dimensional superimposed image presents at least one two-dimensional superimposed region according to the viewing direction;

wherein the method further comprises adjusting a number of images of the portion of the one or more two-dimensional images superimposed along the viewing direction according to a contour sharpness of the at least one two-dimensional superimposed region in the two-dimensional superimposed image;

wherein the portion of the one or more two-dimensional images contains a three-dimensional pedicle region.

* * * * *